US008467856B2

(12) United States Patent
Renisch et al.

(10) Patent No.: US 8,467,856 B2
(45) Date of Patent: Jun. 18, 2013

(54) ANATOMY MODELING FOR TUMOR REGION OF INTEREST DEFINITION

(75) Inventors: Steffen Renisch, Hamburg (DE); Roland Opfer, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 52 days.

(21) Appl. No.: 13/384,342

(22) PCT Filed: Jun. 15, 2010

(86) PCT No.: PCT/IB2010/052689
§ 371 (c)(1),
(2), (4) Date: Jan. 17, 2012

(87) PCT Pub. No.: WO2011/010231
PCT Pub. Date: Jan. 27, 2011

(65) Prior Publication Data
US 2012/0123253 A1    May 17, 2012

Related U.S. Application Data

(60) Provisional application No. 61/226,393, filed on Jul. 17, 2009.

(51) Int. Cl.
*A61B 5/05* (2006.01)
(52) U.S. Cl.
USPC ........... 600/431; 600/407; 600/409; 600/410; 382/130; 382/131; 382/132
(58) Field of Classification Search
USPC ............... 600/407–436; 382/130–132
See application file for complete search history.

(56) References Cited

U.S. PATENT DOCUMENTS

| 5,381,791 | A  | * | 1/1995  | Qian ............................ 600/436 |
| 7,024,028 | B1 | * | 4/2006  | Bar Shalev ................... 382/131 |
| 7,574,304 | B2 | * | 8/2009  | Jackway et al. ................ 702/19 |
| 7,711,160 | B2 | * | 5/2010  | O'Donnell et al. ........... 382/128 |
| 7,822,246 | B2 | * | 10/2010 | Senegas et al. ............... 382/128 |
| 2005/0033143 | A1 | * | 2/2005 | O'Donnell et al. ........... 600/407 |
| 2005/0058322 | A1 | * | 3/2005 | Farmer et al. ................. 382/103 |

(Continued)

OTHER PUBLICATIONS

Blaffert, T., et al.; Hot spot detection, segmentation, and identification in PET images; 2006; Proc. of SPIE; vol. 6144; pp. 614457-1-614457-8.

(Continued)

*Primary Examiner* — Sanjay Cattungal

(57) ABSTRACT

A hot spot detection system for automatically segmenting and quantifying hot spots in functional images includes a segmentation unit (76) to segment an anatomical image representation (72) into regions corresponding to anatomical structures of a subject. A hot spot detection unit (90) detects regions of high uptake from a functional second image representation (74). The regions of high tracer uptake indicate high metabolic activity which maybe caused by potentially hazardous tumor lesions or other malignant processes. However, a number of normally functioning organs uptake high amounts of imaging tracer, particularly FDG. Therefore, a suppression unit (102) suppresses regions of high tracer uptake in the functional second image representation based on the results of a classification unit (101). The classification unit classifies the regions of high tracer uptake according to their position relative to the anatomical structures segmented from the anatomical first image representation. The remaining un-suppressed regions of high uptake are identified by an identification unit (106) as one of potential lesion and non-potential lesion.

19 Claims, 5 Drawing Sheets

U.S. PATENT DOCUMENTS

2005/0261577 A1* 11/2005 Ficaro et al. .................. 600/425
2007/0081712 A1 4/2007 Huang et al.
2008/0050000 A1 2/2008 Blaffert et al.

OTHER PUBLICATIONS

Guan, H., et al.; Automatic Hot Spot Detection and Segmentation in Whole Body FDG-PET Images; 2006; IEEE Int'l Conf. Image Processing; pp. 85-88.

Han, J., et al.; Computer-aided evaluation of anatomical accuracy of image fusion between X-ray CT and SPECT; 2008; Computerized Medical Imaging and Graphics; 32(5)388-395.

Kanakatte, A., et al.; A Pilot Study of Automatic Lung Tumor Segmentation from Positron Emission Tomography Images using Standard Uptake Values; 2007; Computational Intelligence in Image and Signal Processing; pp. 363-368.

Kikinis, R., et al.; A Digital Brain Atlas for Surgical Planning, Model-Driven Segmentation, and Teaching; 1996; IEEE Trans. on Visualization and Computer Graphics; 2(3)232-241.

Schillaci, O., et al.; Single-Photon Emission Computed Tomography/Computed Tomography in Abdominal Diseases; 2006; Seminars in Nuclear Medicine; 37(1)48-61.

Van Kriekinge, S. D., et al.; Tumor Quantitation and Monitoring in Whole-Body Planar Technetium-99m-Sestamibi Imaging; 1997; J. of Nuclear Medicine; 38(3)356-361.

Zhan, Y., et al.; Towards Organ-specific PET-CT Interpretation: Generic Organ Segmentation Using Joint PET-CT Information; 2008; Proc. of First Workshop on Analysis of Functional Medical Images; pp. 113-120.

* cited by examiner

ANATOMY MODELING FOR TUMOR REGION OF INTEREST DEFINITION

CROSS REFERENCE TO RELATED APPLICATIONS

This application claims the benefit of U.S. provisional application Ser. No. 61/226,939 filed Jul. 20, 2009, which is incorporated herein by reference.

The present application relates to diagnostic imaging systems and methods. It finds particular application in conjunction with Positron Emission Tomography (PET) multi-modality imaging systems and will be described with particular reference to hot spot detection of multi-focal diseases and lesion quantification.

Nuclear medicine imaging employs a source of radioactivity to image a patient. Typically, a radiopharmaceutical is injected into the patient. Radiopharmaceutical compounds contain a radioisotope that undergoes decay at a predictable rate and emits or causes the emission of gamma (γ) rays of a characteristic energy. One or more radiation detectors are placed adjacent to the patient to monitor and record emitted radiation. Sometimes, the detector is rotated or indexed around the patient to monitor the emitted radiation from a plurality of directions. Based on information such as detected position and energy, the radiopharmaceutical distribution in the body is determined and an image of the distribution is reconstructed to study the circulatory system, radiopharmaceutical uptake in selected organs or tissue, and the like.

Nuclear medicine imaging has been increasingly used in cancer imaging due to the success of the tracer [18F]-fluorodeoxyglucose (FDG). Focal areas of abnormally increased FDG uptake are known as hot spots and display as regions of high local intensity in PET images. The hot spots indicate a region of high metabolic activity, which may be a result of tumor lesions or other malignant processes. Accurate and reliable quantification of lesion activity in PET images is essential for patient staging as well as monitoring the response to treatment for many cancer types.

In order to assess the images, in the current clinical practice a clinician manually marks and segments lesions, which are assumed to be indicative of the entire disease. However, multi-focal diseases such as lymphoma and other diseases with lymph node involvement and metastases, the number of foci might be too large. Due to time constraints, usually three lead lesions are defined. However, indicative lesions are often obscured by non-pathological tracer uptake of normal anatomical structures. In the case of FDG-PET, normally functioning organs with high metabolic activity such as the heart, brain, bladder, liver, K, or the like often show FDG uptake unrelated to cancer. Additionally, Partial volume effects (PVE) pose another problem for identifying tumor lesions in PET images.

Often, the PET images are combined with the computed tomography (CT) images, magnetic resonance (MR) images, or other images of the same anatomical region. The present application provides a new and improved PET imaging system and method which overcomes the above-referenced problems and others.

In accordance with one aspect, a hot spot detection system includes a segmentation unit which segments an anatomical first image representation into regions corresponding to anatomical structures of a subject and a hot spot detection unit which detects regions of high uptake from a functional second image representation. A classification unit classifies the regions of high tracer uptake according to their position relative to the anatomical structures segmented from the anatomical first image representation. A suppression unit suppresses regions of high tracer uptake in the functional second image representation based on the results of the classification unit. An identification unit identifies unsuppressed regions of high uptake as one of potential lesion and non-potential lesion.

In accordance with another aspect, a method for diagnostic imaging includes segmenting an anatomical first image representation into regions corresponding to anatomical structures and detecting from a functional second image representation a plurality of regions of high tracer uptake. Regions of high uptake in the functional second image representation that correspond with one or more segmented regions of the segmented anatomical first image representation are suppressed. And, unsuppressed regions of high uptake are indentified as one of potential and non-potential lesions.

In accordance with a third aspect, anatomical regions identified in the anatomical first image representation could be carried over to the functional second image representation in order to delineate anatomical structures there. The tracer uptake in these structures could be used as a reference for the quantification of the hot spots, e.g. the relative activity of a hot spot compared with that of normal liver tissue could be computed.

One advantage relies in that automatic detection and quantification of lesions is improved.

Another advantage relies in that time of identification of lesions is improved

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 1 diagrammatically shows a diagnostic imaging system employing a hot spot detection system;

FIG. 2 diagrammatically shows a hot spot detection system;

Figure 1:
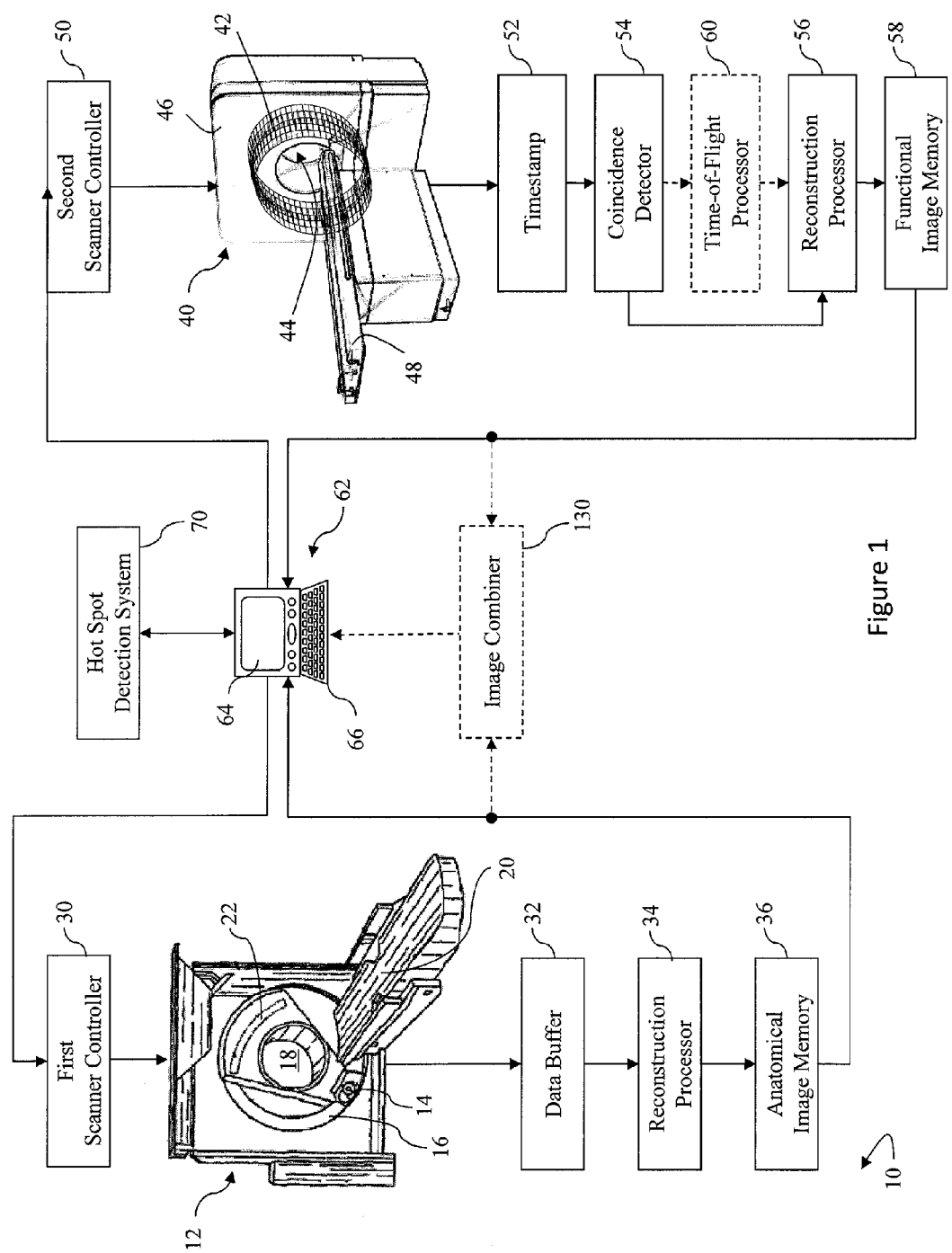

With reference to FIG. 1, a diagnostic system 10 includes a first imaging system, a diagnostic imaging scanner 12 such as a computed tomography (CT) imaging scanner, an MRI scanner, or the like for obtaining anatomical diagnostic images. In the illustrated embodiment, the diagnostic imaging scanner 12 includes an x-ray source 14 mounted on a rotating gantry 16. The x-ray source 14 produces x-rays passing through an examination region 18, where they interact with a target area of a subject (not shown) supported by a support 20 which positions the target area within the examination region 18. An x-ray detector array 22 is arranged to receive the x-ray beam after it passes through the examination region 18 where the x-rays interact with and are partially absorbed by the subject. The detected x-rays therefore include absorption information relating to the subject.

The CT scanner 12 is operated by a controller 30 to perform selected imaging sequences of a selected target area. The imaging sequences acquire diagnostic imaging data of the target area. The diagnostic imaging data is stored in a data buffer 32. A reconstruction processor 34 reconstructs 3D image representations from the acquired imaging data, and the reconstructed image representations are stored in a diagnostic anatomical image memory 36.

The diagnostic system 10 includes a second imaging system, particularly a functional imaging scanner 40 such as a PET scanner, SPECT scanner, or the like for obtaining functional images. In the illustrated embodiment, the functional imaging scanner 40, which is illustrated as a PET scanner, includes a plurality of radiation detector modules 42 oriented to receive γ radiation from an imaging region 44. The radiation detector modules 42 are arranged in several adjacent rings along an axial direction as depicted; however, other arrangements of radiation detector modules can be used. The radiation detector modules 42 are typically housed within a housing 46 of the tomography scanner 40 and thus are not visible from the outside. Typically, each ring is comprised of hundreds or thousands of radiation detector modules 42. The functional imaging scanner 40 includes a subject support 48 for positioning an object or a human patient in the imaging region 44. The support 48 is linearly movable in the axial direction generally transverse to the rings of the radiation detector modules 42 to facilitate acquisition of three-dimensional imaging data over an extended axial distance.

The PET scanner 40 is operated by a controller 50 to perform selected imaging sequences of a selected target area. Typically, an object or patient to be imaged is injected with one or more radiopharmaceutical or radioisotope tracers and placed in the examination region 44 supported by the support 48. Examples of such tracers are 18F FDG, C-11, Tc-99m, Ga67, and In-111. The presence of the tracer within the object produces emission radiation from the object. Radiation events are detected by the detector modules 42 around the examination region 44. A time stamp is associated with each detected radiation event by a time stamp circuit 52. A coincidence detector 54 determines coincident pairs of γ rays and the line of responses (LOR) defined by each coincident pair of γ rays based on differences in detection time of the coincidence pairs and the known diameter of the field of view. A reconstruction processor 56 reconstructs all the LORs into an image representation which is stored in a functional image memory 58. Optionally, a time-of-flight processor 60 localizes each radiation event by deriving time-of-flight information from the timestamps for each LOR. A workstation or graphic user interface 62 includes a display device 64 and a user input device 66 which a clinician can use to select scanning sequences and protocols, display image data, and the like.

Although the anatomical and functional scanners are illustrated separate, it is to be appreciated that they can be combined. In one embodiment, the anatomical and functional scanners are connected contiguous to each other with the central axes of their imaging regions aligned. A common support moves the object or patient sequentially through the imaging regions. In another embodiment, the anatomical and functional scanners share a common housing and a common imaging region. For example, the PET detectors can surround the imaging volume and an MRI magnet and gradient magnetic field coils and RF transmit and/or receive coils can be disposed around, inside of, and up or downstream from the ring of PET detectors. Similar combined PET/CT, SPECT/CT, SPECT/MRI, PET/ultrasound, etc. scanners are also contemplated.

Figure 2:
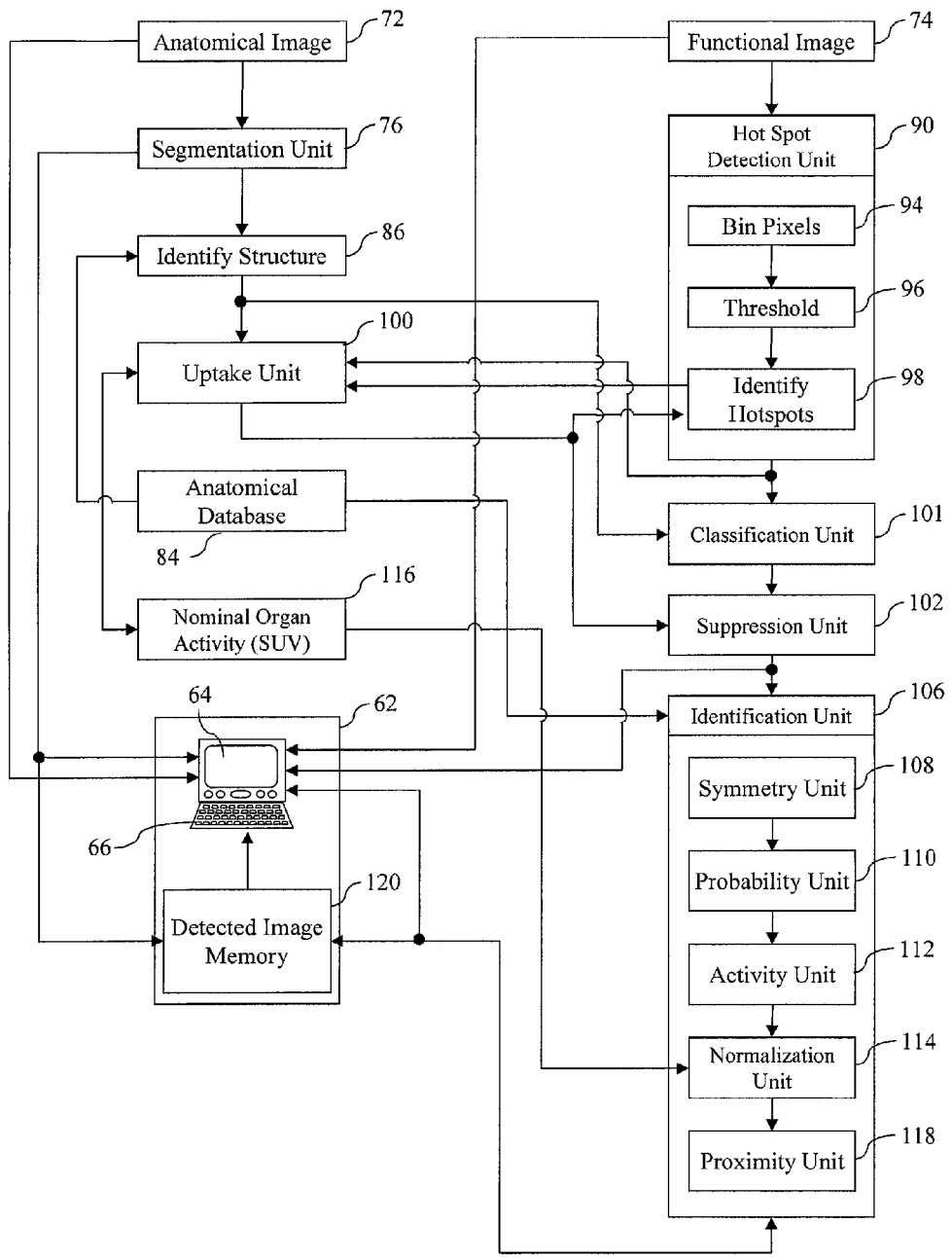
Figure 3C:
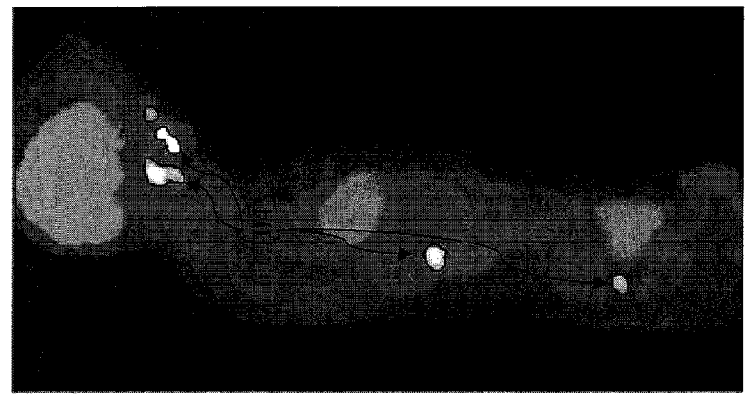
FIG. 3C illustrates regions of high intensity after anatomical structures are suppressed.
Figure 3B:
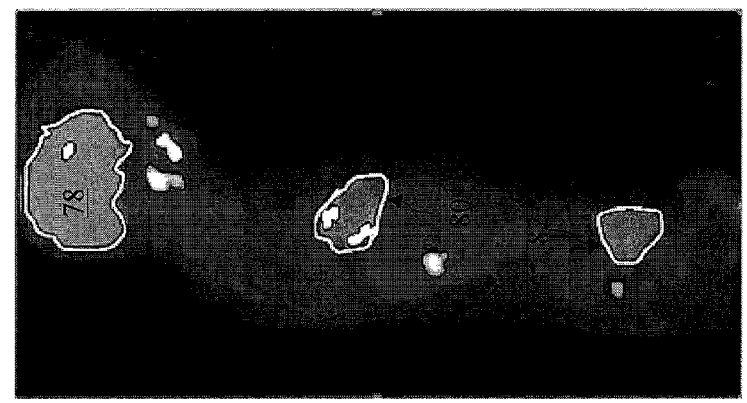
FIG. 3B illustrates anatomical structures segmented in an anatomical image representation.

Continuing with reference to FIG. 1 and further reference to FIGS. 2 and 3B, the diagnostic system 10 includes a hot spot detection system 70 for automatic detection of a region of interest (ROI) pertaining to a lesion and automatic quantification of metabolic activity in detected lesions based on anatomical images 72 from the anatomical image memory 36 and functional images 74 from the functional image memory 58. A segmentation unit 76 segments the anatomical first image representation 72 into regions which correspond to anatomical structures, particularly anatomical structures with high radiopharmaceutical tracer uptake which may obscure potential lesions of interest. In the case of FDG-PET, the brain 78, the heart 80, and the bladder 82 are organs of FIG. 3B which, when functioning normally, are examples of anatomical structures which often show high uptake unrelated to cancer. Other organs with high uptake include the kidneys and liver which are also contemplated for segmented anatomical structures. Segmentation can also be helpful for accurately determining a location of the hot spots relative to the patient's anatomy.

While the anatomical image representation 72 and the functional image representation 74 have been so far exemplified as different types of image representations, they can hypothetically be identical. They can be both PET, SPECT, CT, MR, or the like image representations.

The segmentation unit 76 is capable of employing different types of segmentation methods. For example, the segmentation unit 76 can employ a model-based segmentation in which the central assumption is that the anatomical structures of interest have, to some extent, relatively consistent forms of geometry and position across patients. A library of three-dimensional anatomical structure models explaining the shape, geometrical location, size, and variations thereof are defined in an anatomical database 84 prior to the segmentation. During segmentation, the models act as templates to identify 86 and define the boundary of the structure of interest. It is to be appreciated, however, that other segmentation methods such as clustering, edge detection, region growing, principle components analysis, neural network, and the like are also contemplated.

The segmentation unit 76 can also employ an atlas of normal anatomical structures which is mapped to the actual anatomical image. In such an embodiment, the atlas includes the anatomical database 84.

Figure 3A:
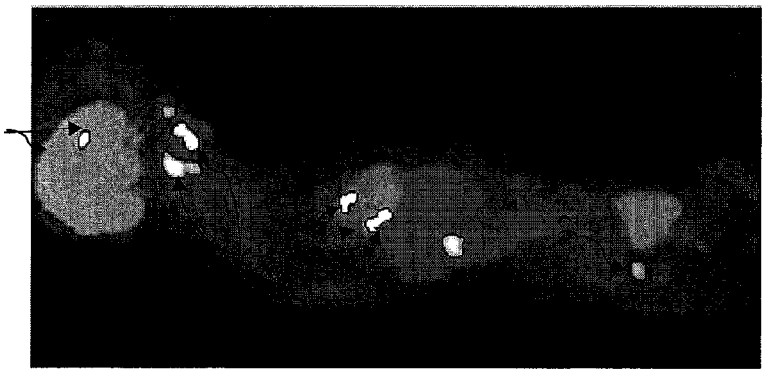
FIG. 3A illustrates regions of high intensity in a functional image representation.
Figure 4:
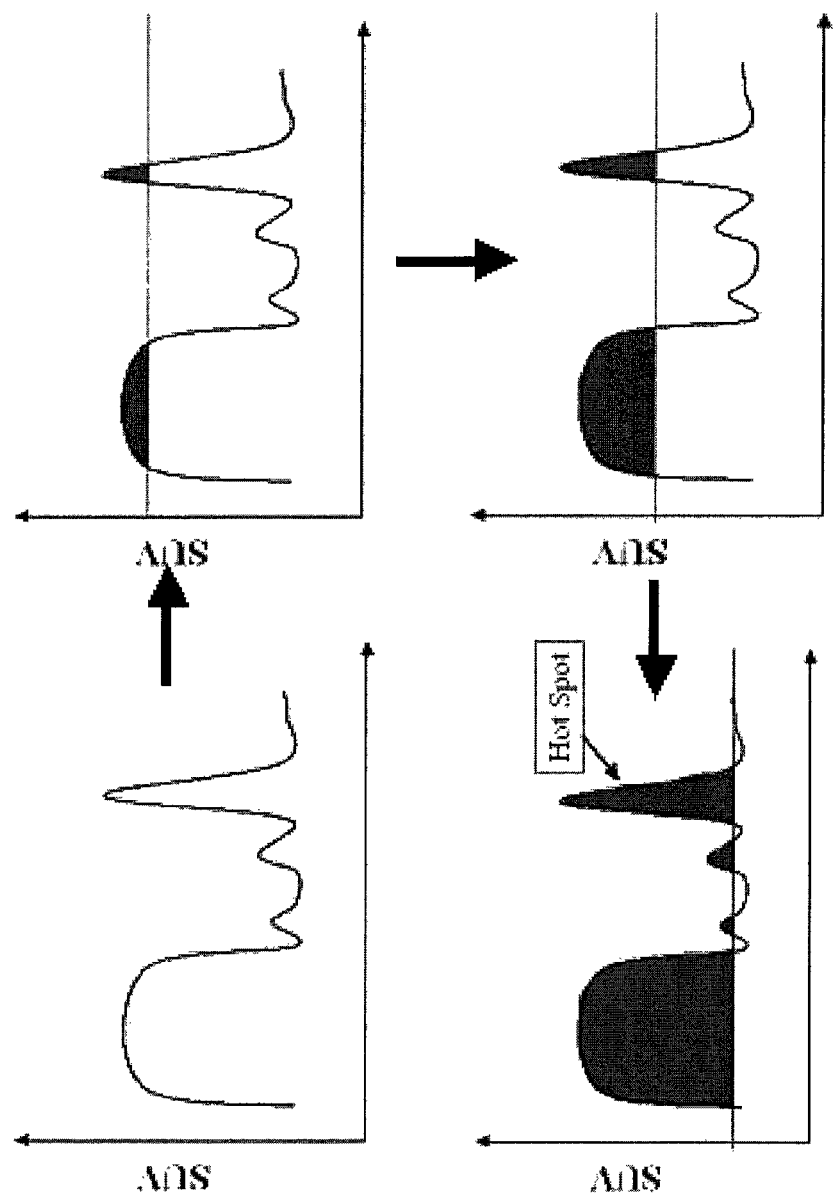
FIG. 4 illustrates a watershed algorithm.

With continuing reference to FIG. 2 and further reference to FIGS. 3A and 4, a hot spot detection unit 90 detects from the functional second image representation 74 regions of high intensity 92, depicted in FIG. 3A. The regions of high intensity 92, generally referred to as hot spots, are regions in the functional second image representation that indicate high metabolic activity, which potentially can be caused by tumor growth or by other malignant processes. These regions of high intensity also include normal functioning structures/organs such as the heart, bladder, kidney, liver, and brain. The regions of high intensity 92 are detected, for example, by a watershed algorithm. A bin sorting unit, processor, or algorithm 94 sorts all the voxels of the second image representation 74 according to grayscale values. Basins with the highest grayscale values are effectively flooded, as depicted in FIG. 4. For each basin, a measure of the compactness of the basin-region and the amplitude between the highest and the lowest grayscale values within the basin is computed. Basins which exceed a certain threshold 96 are highlighted as regions of high intensity 92 with a color overlay. An identification unit, processor, or algorithm 98 uses anatomical information, such as size, shape, location, or the like, from the anatomical database 84 to identify the regions with high tracer uptake, for example as a salivary gland. It should be appreciated that other detection algorithms for detecting regions of high intensity are also contemplated.

With continuing reference to FIG. 2, an uptake unit, processor, or algorithm 100 examines the segmented regions 78, 80, 82 of the first image representation to determine whether the anatomical structure is functioning normally or abnormally based on, for example, at least one of homogeneity and uptake. The uptake unit 100 correlates metabolic activity from the functional image representation 74 corresponding to the segmented regions of the anatomical image representation 72 to determine an uptake value, particularly a standardized uptake value (SUV), a measure of the concentration of the radiopharmaceutical tracer. A segmented region with a consistent uptake value throughout the segmented region and an average uptake value consistent with a predefined level is considered normal.

A classification unit, processor, or algorithm 101 classifies the regions of high tracer uptake according to their position relative to the anatomical structures segmented from the anatomical first image representation. A suppression unit, processor, or algorithm 102 uses the results of the classification unit to suppress the regions of high intensity 92 in the functional second image representation 74. As previously noted, regions of high intensity that correspond to normally functioning anatomical structures may obscure potentially hazardous lesions. To improve detection of potential lesions, normally functioning anatomical structures are suppressed from the functional second image representation while unsuppressed regions 104, shown in FIG. 3C, of high intensity are further analyzed to determine if they are plausible lesions. It should also be noted that suppressing abnormally functional anatomical structures is also contemplated.

An identification unit, processor, or algorithm 106 is configured to calculate metrics corresponding to the unsuppressed regions. The metrics include, but are not limited to, total tumor burden, glycolytic volume, SUV, average activity, maximum activity, minimum activity, homogeneity, and the like. In addition to calculating metrics, the quantification unit includes a number of modules that perform various checks on the unsuppressed regions 104 to determine if they are lesions. For example, a symmetry unit, processor, or algorithm 108 determines symmetric pairs of the high intensity regions of the second and/or first image representation that correspond to paired anatomical structures. For example, if a high intensity region is identified, by the identification unit 98, as a salivary gland, the symmetry unit searches for the corresponding salivary gland on the other side of the patient. Activity patterns between the symmetric pairs are determined by an activity unit, processor, or algorithm 110. If an asymmetry of metabolic activity exists between the symmetric pair, the unsuppressed high intensity region 104 is identified as a potential lesion.

In another embodiment, the results of the identification unit 106 are visualized on the display device 64. The user is asked to confirm or edit the selected hot spots, i.e. high uptake regions, using the input device 66 before a summary report is generated.

The quantification unit also includes a probability unit, processor, or algorithm 112 which determines a probability for a high intensity region in the second image representation whether a lymph node is present. Assessing lymph nodes, such as axillary or mediastinal, is a critical component in determining whether a tumor is likely to have metastasized, which dictates the therapeutic options for cancer patients. A normalization unit, processor, or algorithm 114 compares the metabolic activity of an unsuppressed high intensity region with normally functioning structures, e.g. those identified by the uptake unit 100. For example, metabolic activity of a potential lesion is commonly compared to a standard uptake value determined by a nominal activity unit, processor, or algorithm 116. The nominal activity unit is also capable of determining total tumor burden, total glycolytic volume, or the like. The metabolic activity of the liver can be used as a reference for comparison. Since the liver is segmented and indentified by the segmentation unit 76, an unsuppressed high intensity region can easily be compared to the uptake in the liver. Previously, a clinician had to manually delineate a region of the liver on a workstation which is time consuming and highly subjective. The anatomical regions identified in the anatomical first image representation 72 can be carried over to the functional second image representation 74 in order to delineate anatomical structures in the second image representation 74. The tracer uptake in these structures could be used as a reference for the quantification of the hot spots, e.g. the relative activity of a hot spot compared with that of normal liver tissue could be computed.

The quantification unit also includes a proximity unit 118 which identifies high intensity regions, based on models stored in the anatomy database 84, in close proximity to suppressed regions. The proximity units makes use of anatomical information, provided by the anatomical database 84, to determine where high intensity regions are likely to occur and not occur. This can be translated to the suppression unit and/or segmentation unit to adjust suppressed regions include or exclude regions. For example, if a lymph node is a located close to the heart, a priori knowledge of heart models and lymph node models is used to ensure that the lymph node has not been included in the segmented heart, thus suppressed in the second image representation.

The segmented and unsegmented anatomical images, the function images, the functional image with high uptake organs suppressed, in image or map of quantified hot spots, and superimposed combinations thereof are stored in a detected image memory 120 of a workstation or graphic user interface 62.

With returning reference to FIG. 1, an optional image combiner 130 combines the anatomical first image representation and the functional second image representation into a combined image for concurrent display. For example, the images can be superimposed in different colors, the outline of the functional second image representation hotspots can be superimposed on the first image representation, the outline of the segmented anatomical structures of the anatomical first image representation can be superimposed on the functional second image representation, the first and second image representations can be displayed side by side with a common scale, or the like.

Figure 5:
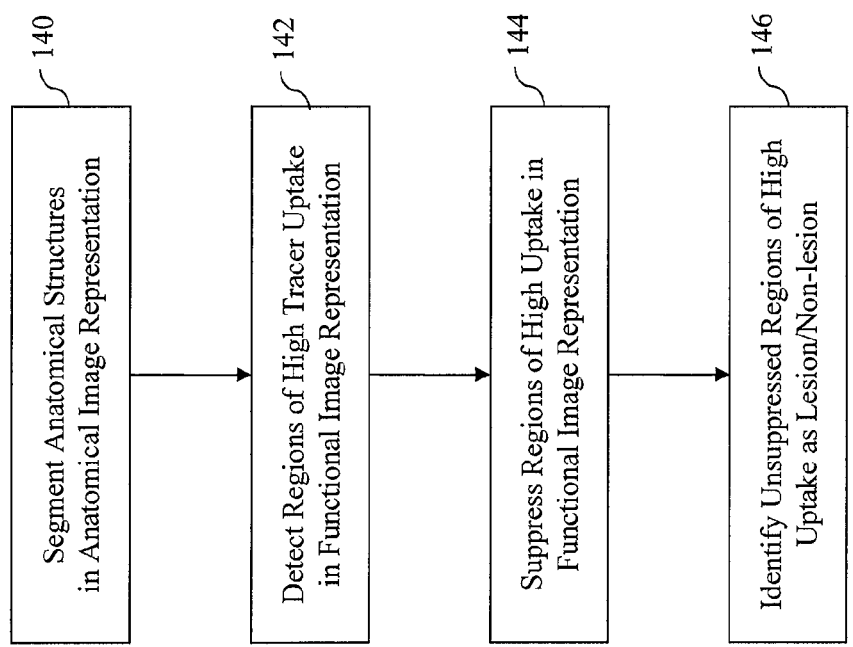
FIG. 5 is a flow chart depicting a method for detecting regions of high uptake.

With reference to FIG. 5, a method for diagnostic imaging includes segmenting 140 an anatomical first image representation into regions corresponding to anatomical structures and detecting 142 from a functional second image representation a plurality of regions of high tracer uptake. Regions of high uptake in the functional second image representation that correspond with one or more segmented regions of the segmented anatomical first image representation are suppressed 144. And, unsuppressed regions of high uptake are indentified 146 as one of potential and non-potential lesions.

The invention has been described with reference to the preferred embodiments. Modifications and alterations may occur to others upon reading and understanding the preceding detailed description. It is intended that the invention be construed as comprising all such modifications and alterations insofar as they come within the scope of the appended claims or the equivalents thereof.

Having thus described the preferred embodiments, the invention is now claimed to be:

1. A hot spot detection system, including:
   a segmentation unit which segments an anatomical first image representation into regions corresponding to anatomical structures of a subject;
   a hot spot detection unit which detects regions of high tracer uptake from a functional second image representation;
   a classification unit which classifies the regions of high tracer uptake according to their position relative to the anatomical structures segmented from the anatomical first image representation;
   a suppression unit which suppresses regions of high tracer uptake in the functional second image representation based on results of the classification unit; and
   an identification unit which identifies unsuppressed regions of high uptake as one of potential lesion and non-potential lesion.

2. The hot spot detection system according to claim 1, wherein the segmentation unit identifies and segments the anatomical structure based on a priori information according to at least one of shape, size, and geometrical location of the anatomical structure.

3. The hot spot detection system according to claim 1, further including:
   an uptake unit which examines segmented regions of first image representation for at least one of homogeneity and uptake to identify normal and abnormal regions.

4. The hot spot detection system according to claim 3, wherein the suppression unit suppresses the regions of the functional image representation that corresponds to anatomical structures identified as normal.

5. The hot spot detection system according to claim 1, further including:
   a probability unit which determines a probability of the high uptake regions of the functional image representation corresponding to a lymph node.

6. The hot spot detection system according to claim 1, further including:
   a symmetry unit which determines symmetric pairs of the high uptake regions of the functional image representation that correspond to paired anatomical structures; and
   an activity unit which compares metabolic activity between the determined symmetric pairs of high uptake regions to identify asymmetry in metabolic activity.

7. The hot spot detection system according to claim claim 1, further comprising:
   a nominal activity unit which determines a metric for the unsuppressed high intensity regions based on any one of total tumor burden, total glcolytic volume, and standardized uptake value.

8. The hot spot detection system according to claim 7, wherein the nominal activity unit determines a nominal metabolic activity in a selected segmented region.

9. The hot spot detection system according to claim 8, wherein the selected segmented region corresponds to a liver.

10. The hot spot detection system according to claim 1, wherein the hot spot detection unit detects regions of high uptake using a watershed transform.

11. The hot spot detection system according to claim 1, further including:
    a workstation that outlines the detected regions of high uptake with a color overlay and displays the detected regions of high uptake on a display device.

12. The hot spot detection system according to claim 1, wherein the regions of high uptake indicate high metabolic activity.

13. A diagnostic imaging system, comprising:
    an anatomical image scanner configured to generate an anatomical first image representation;
    a positron emission tomography (PET) scanner configured to generate a functional second image representation; and
    a hot spot detection system according to claim 1.

14. A method for diagnostic imaging, including:
    segmenting a anatomical first image representation into regions corresponding to anatomical structures;
    detecting from a functional second image representation a plurality of regions of high tracer uptake;
    classifying the regions of high tracer uptake according to their position relative to the anatomical structures segmented from the anatomical first image representation;
    suppressing regions of high uptake in the functional second image representation based on the classification of the high tracer uptake regions; and
    identifying unsuppressed regions of high uptake as one of potential lesion and non-potential lesion.

15. The method according to claim 14, further including:
    determining symmetric pairs of the high uptake regions of the second image representation that correspond to paired anatomical structures based on anatomical information; and
    comparing metabolic activity between the determined symmetric pairs of high uptake regions to identify asymmetry in metabolic activity.

16. The method according to claim 14, further including:
    normalizing metabolic activity levels of the unsuppressed regions of high uptake with a nominal intensity in a selected segmented region.

17. The method according to claim 14, wherein segmenting the anatomical structure is based on a priori information according to at least one of shape, size, and geometrical location of the anatomical structure.

18. The method according to claim 14, wherein the functional image representation is generated by a PET imaging scanner.

19. The method according to claim 14, wherein the unsuppressed regions of high uptake are displayed.

* * * * *